U S008580886B2

(12) United States Patent
Backer et al.

(10) Patent No.: US 8,580,886 B2
(45) Date of Patent: Nov. 12, 2013

(54) METHOD FOR THE PREPARATION AND USE OF BIS (ALKOXYSILYLORGANO)-DICARBOXYLATES

(75) Inventors: Michael Backer, Mainz (DE); John Gohndrone, Midland, MI (US); Don Kleyer, Hemlock, MI (US); Xiaobing Zhou, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/310,004

(22) Filed: Dec. 2, 2011

(65) Prior Publication Data

US 2013/0072625 A1 Mar. 21, 2013

Related U.S. Application Data

(63) Continuation-in-part of application No. PCT/US2011/052331, filed on Sep. 20, 2011.

(51) Int. Cl.
*C08K 5/5419* (2006.01)
*C07F 7/18* (2006.01)

(52) U.S. Cl.
USPC .......................................... 524/576; 556/440

(58) Field of Classification Search
USPC ........................................... 524/576; 556/440
See application file for complete search history.

(56) References Cited

U.S. PATENT DOCUMENTS

| | | | |
|---|---|---|---|
| 3,179,612 | A | 4/1965 | Plueddemann, et. al. |
| 3,307,967 | A | 3/1967 | Vanderbilt, et. al. |
| 3,443,620 | A | 5/1969 | Vanderbilt, et. al. |
| 3,769,244 | A | 10/1973 | Hashimoto, et. al. |
| 4,281,145 | A | 7/1981 | Mitchell |
| 4,465,867 | A | 8/1984 | Maekawa et al. |
| 4,465,868 | A | 8/1984 | Maekawa et al. |
| 4,496,682 | A | 1/1985 | Schmiegel |
| 4,524,104 | A | 6/1985 | Hagio et al. |
| 4,845,259 | A | 7/1989 | Arai et al. |
| 4,910,260 | A | 3/1990 | Wachi et al. |
| 4,946,977 | A | 8/1990 | Bernhardt et al. |
| 5,041,194 | A | 8/1991 | Mori et al. |
| 5,041,593 | A | 8/1991 | Plueddemann |
| 5,082,968 | A | 1/1992 | Brunelle |
| 5,089,300 | A | 2/1992 | Plueddemann |
| 5,117,027 | A | 5/1992 | Bernhardt et al. |
| 5,274,184 | A | 12/1993 | Nagl et al. |
| 5,409,998 | A | 4/1995 | Chiodini et al. |
| 5,451,625 | A | 9/1995 | Fukushi |
| 5,658,671 | A | 8/1997 | Fukushi |
| 5,684,065 | A | 11/1997 | Hiraoka et al. |
| 5,712,407 | A | 1/1998 | Kreutzberger et al. |
| 5,811,479 | A | 9/1998 | Labauze |
| 5,870,275 | A | 2/1999 | Shiono et al. |
| 5,905,150 | A * | 5/1999 | Simonian et al. ............. 544/221 |
| 5,959,037 | A | 9/1999 | Saito et al. |
| 6,071,995 | A | 6/2000 | Labauze |
| 6,114,473 | A | 9/2000 | Miyake et al. |
| 6,262,879 | B1 | 7/2001 | Nitta et al. |
| 6,329,471 | B1 | 12/2001 | Mizuide et al. |
| 6,448,427 | B1 | 9/2002 | Wakita et al. |
| 6,608,225 | B1 | 8/2003 | Larson et al. |
| 6,815,554 | B2 | 11/2004 | Pfeiffer et al. |
| 6,900,263 | B2 | 5/2005 | Hodge |
| 6,903,155 | B2 | 6/2005 | Hodge |
| 7,078,449 | B2 | 7/2006 | Pagano et al. |
| 7,186,776 | B2 | 3/2007 | Tardivat et al. |
| 7,256,233 | B2 | 8/2007 | Simonot et al. |
| 7,262,312 | B2 | 8/2007 | Sheridan et al. |
| 7,271,228 | B2 | 9/2007 | Armand et al. |
| 7,300,970 | B2 | 11/2007 | Durel et al. |
| 7,629,408 | B2 | 12/2009 | Cambon et al. |
| 7,718,717 | B2 | 5/2010 | Lapra et al. |
| 7,758,897 | B2 | 7/2010 | Roettger et al. |
| 7,851,627 | B2 | 12/2010 | Mezei et al. |
| 2003/0163000 | A1 | 8/2003 | Atkinson et al. |
| 2009/0134354 | A1 | 5/2009 | Dubois et al. |
| 2009/0173907 | A1 | 7/2009 | Dubois et al. |
| 2009/0235574 | A1 | 9/2009 | Earle et al. |
| 2010/0048829 | A1 | 2/2010 | D'Andola et al. |
| 2010/0310853 | A1 | 12/2010 | Schwiegk et al. |
| 2010/0311918 | A1 | 12/2010 | Toufaili et al. |
| 2011/0065926 | A1 | 3/2011 | Maase et al. |
| 2011/0077435 | A1 | 3/2011 | Sato et al. |
| 2011/0190411 | A1 | 8/2011 | Backer et al. |

FOREIGN PATENT DOCUMENTS

| | | |
|---|---|---|
| JP | 05-306290 | 11/1993 |
| JP | 2009-007565 | 1/2009 |
| JP | 2010-150461 A1 | 7/2010 |

(Continued)

OTHER PUBLICATIONS

Aziz, et. al. "Cation-Specific Interactions with Carboxylate in Amino Acid and Acetate Aqueous Solutions: X-ray Absorption and ab initio Calculations", Journal of Physical Chemistry B Letters, 2008, 12567-12570, 112.

Baidya, Mahiuddin, "Nucleophilicites and Lewis Basicities of Tertiary Amines: A Key to Rationalize Nucleophilic Organocatalysis", Ludwig-Maximillians University, Thesis, 2009, Karalirchack, India.

Chen, Xinzhi, et. al. "DBU Derived Ionic Liquids and Their Application in Organic Synthetic Reactions", School of Pharmaceutical and Chemical Engineering, 305-330, 14, Taizhou University, Taizhou, P.R. China.

Hajipour, et. al. "Basic Ionic Liquids. A Short Review", J. Iran. Chem. Soc., Dec. 4, 2009, pp. 647-678, vol. 6, No. 4.

Im, Yang., et. al. "Nucleophilic Behaviour of DBU and DBN toward Acetylated Baylis-Hillman Adducts", Bull. Korean Chem. Soc., 2001, 1053-1055, vol. 22, No. 9, Chonnam National Univeristy, Kwangju, Korea.

(Continued)

*Primary Examiner* — Robert D. Harlan
(74) *Attorney, Agent, or Firm* — Matthew T. Fewkes

(57) ABSTRACT

A method for preparing a bis(alkoxysilylorgano)dicarboxylate includes reacting a haloorganoalkoxysilane, a dimetal salt of a dicarboxyl functional compound, and a phase transfer catalyst. A quaternary iminium compound of a polyaza, polycycloalkene is useful as the phase transfer catalyst. The product may be a bis(alkoxysilylalkyl)fumarate, which is useful as a coupling agent in rubber compositions for tire applications.

21 Claims, No Drawings

(56) References Cited

FOREIGN PATENT DOCUMENTS

| | | | |
|---|---|---|---|
| JP | 2010-256863 A1 | 11/2010 | |
| JP | 2011-148711 A1 | 4/2011 | |
| PL | 182004 B1 | 7/1998 | |
| WO | 2005/103061 A1 | 11/2005 | |
| WO | WO 2005/103061 | * | 11/2005 |
| WO | 2006/111712 A2 | 10/2006 | |
| WO | 2007/118923 A1 | 10/2007 | |
| WO | 2010/000834 A1 | 1/2010 | |
| WO | 2010/040653 A1 | 4/2010 | |
| WO | 2010/046608 A9 | 4/2010 | |
| WO | 2010/125123 A1 | 11/2010 | |
| WO | 2010/125124 A1 | 11/2010 | |

OTHER PUBLICATIONS

Kuo, et. al., "Inverse Phase Transfer Catalysis. Kinetics and Mechanism of the Pyridine 1-Oxide-Catalyzed Substitution Reaction of Benzoyl Chloride and Benzoate Ion in a Two-Phase Water/Dichloromethan Medium", J. Org. Chem., 1992, 1991-1995, vol. 57, National Cheng Kung University, Tainan, Taiwan.
Sobral, et. al., "Synthesis and crystal structure of new phase-transfer catalysts based on 1,8-diazabicyclo[5.4.0] undec-7-ene and 1,5-diazabicyclo[4.3.0]non-5-ene", Progr. Colloid Polym. Sci, 2004, 28-30, 123, Springer-Verlag.
Vlachy, et. al., "Hofmeister series and specific interactions of charged headgroups with aqueous ions", Advances in Colloid and Interface Science, 2008, 1-6, Regensburg, Germany.
Ying, et. al., "Green and efficient aza-Michael additions of aromatic amines to a,b-unsaturdated ketones catalyzed by DBU based task-specific ionic liquids without solvent", Arkat USA, Inc., 288-298.
JP 09-124760, "Production of Rigid Polyisocyanurate Foam", abstract only.
JP 09-137149, "Hot-Melt Type Acrylic Pressure-Sensitive Adhesive Composition", abstract only.
JP 09-157623, "Acrylic Pressure-Sensitive Adhesive Composition", abstract only.
JP 10-017798, "Catalyst for Magnetic Coating Material and Magnetic Recording Medium", abstract only.
JP 11-050033, "Acrylic Pressure-Sensitive Adhesive Composition", abstract only.
JP 11-054375, "Electric Double Layer Capacitor Melting Type Electrolyte", abstract only.
JP 11-054376, "Electric Double Layer Capacitor", abstract only.
JP 11-054377, "Electric Double Layer Capacitor", abstract only.
JP 11-054379, "Electrolyte and Electrochemical Element Using the Same", abstract only.
JP 11-238653, "Electric Double-Layered Capacitor", abstract only.
JP 56-104890, "Preparation of Organosilane", abstract only.
JP 63-268757, "Composition for Curing Fluoro-Rubber", abstract only.
JP 2000-232037, "Electrolytic Solution", abstract only.
JP 2002-321981, "Dispersant for Ceramic Material", abstract only.
JP 2002-334815, "Electric Double-Layer Capacitor", abstract only.
JP 2003-272956, "Electrolyte for Electrochemical Capacitor", abstract only.
JP 2003-301143, "Resin Composition for Powder Coating Material", abstract only.
JP 2003-324039, "Electric Double-Layer Capacitor and Electrolyte Therefor", abstract only.
JP 2005-197665, "Electrolyte for Electrochemical Capacitor and Electrochemical Capacitor using the Same", abstract only.
JP 2006-089379, "Method for Producing Electrolyte for Electrolytic Solution", abstract only.
JP 2006-104143, "Method for Producing Quaternary Amidinium Salt", abstract only.
JP 2006-156728, "Electrochemical Capacitor and Electrolyte Therefor", abstract only.
JP 2006-206440, "Method for Producing Salt", abstract only.
JP 2007-039653, "Liquid Lubricant", abstract only.
JP 2008-202023, "Lubricant", abstract only.
JP 2008-266556, "Lubricant", abstract only.
JP 2008-266557, "Lubricant", abstract only.
Starks, Charles M., et. al. "Variables in Reaction Design for Laboratory and Industrial Applications of Phase-Transfer Catalysis", Phase-Transfer Catalysis Fundamentals, Applications, and Industrial Perspectives (book), pp. 266-338, Chapman & Hall, 1994.
JP 2010-070539, "Ionic Liquid", abstract only.
JP 2010-138234, "Antistat and Application Thereof", abstract only.
Blanco, Carlos, et. al., "Alkylation of naphthalene using three different ionic liquids", Journal of Molecular Catalysis, Apr. 24, 2006, pp. 203-206.
Fedorynski, Michal, et. al. "Phase transfer catalyzed (PTC) reactions of chloroform with alkenyl carboxylates. Effect of catalyst structure on reaction course", Tetrahedron, vol. 53, Issue 3, Jan. 20, 1997.
Makosza, Mieczyslaw, et. al. "Co-catalysis in phase transfer catalyzed reactions (a concept paper)", Arkivoc 2006 (iv), 7-17, Inst. of Organic Chemistry, Polish Academy of Sciences, Kasprzaka, Warszawa.
Arbin, Astrid, et. al., "Alkylation of carboxylic acids by solid-liquid phase-transfer catalysis for determination by gas chromatography", Journal of Chromatography A., vol. 170, Issue 1, Feb. 11, 1979.
Sirovskii, F.S., et. al. "Inhibition and synergism in phase transfer catalysis" Russian Chemical Reviews, 1991, 60 (4), pp. 345-357.
Kiesewetter, Matthew K., "Cyclic Guanidine Organic Catalysts: What is Magic About Triazabicyclodecene?", J. Org. Chem., 2009, pp. 9490-9496, 74. Supporting documentation included.
Cotton, F. Albert et. al. "Homologus of the Easily Ionized Compound Mo2(hpp)4 Containing Smaller Cicyclic Guanidinates", Inorg. Chem. 2006, 45, pp. 5493-5500.
Coles, Martyn P., "Bicyclic-guanidines, -guanidinates and -guanidinium salts: wide ranging applications from a simple family of molecules", 2009, pp. 3659-3676, The Royal Society of Chemistry.
Ghobril, Cynthia, et. al. "Structure-Reactivity Relationship Studies for Guanidine-Organocatalyzed Direct Intramolecular Aldolization of Ketoaldehydes", ChemCatChem, 2010, 2, 1573-1581, Wiley-VCH.
Lecuyer, Julien, "Organocatalytic decomposition of poly(ethylene terephthalate) using triazabicyclodecene proposal", Master's Theses and Graduate Research, 2010, San Jose State University.
Dehmlow, E.V., "Tetramethylammonium Salts as Phase Transfer Catalysts", SACHEM Inc., 2008.

* cited by examiner

METHOD FOR THE PREPARATION AND USE OF BIS (ALKOXYSILYLORGANO)-DICARBOXYLATES

CROSS-REFERENCE TO RELATED APPLICATIONS AND STATEMENT REGARDING FEDERALLY SPONSORED RESEARCH

This application is a continuation in part of PCT Application No. PCT/US11/52331 filed on 20 Sep. 2011, currently pending, which is hereby incorporated by reference.

TECHNICAL FIELD

A new route to synthesize bis(alkoxysilylorgano)dicarboxylate compounds, such as bis(alkoxysilylalkyl)fumarates, is disclosed. The bis(alkoxysilylalkyl)fumarates, such as bis(triethoxysilylpropyl)fumarate, are useful in tire formulations. The new route may produce the bis(alkoxysilylalkyl) fumarates faster, at a lower temperature, and/or with fewer by-products than conventional methods for producing bis (alkoxysilylalkyl)fumarates.

BACKGROUND OF THE INVENTION

Phase transfer catalyzed reaction of a dimetal dicarboxylate with a haloorganoalkoxysilane can be performed using a quaternary ammonium catalyst, such as benzyltrimethylammonium chloride. However, benzyltrimethylammonium chloride suffers from the drawback of being thermally unstable at temperatures used for this reaction, and thus would not be considered a high performance catalyst. Tetrabutylammonium halides, such as tetrabutylammonium bromide (TBAB), may also be thermally unstable at the temperatures needed to produce the bis(alkoxysilylorgano) dicarboxyl functional compounds. Using TBAB as a phase transfer catalyst may result in catalyst decomposition products, e.g., tributylamine and butylfumarate, being present in the product.

Amine quat salts suffer from being less thermally stable and less efficient (since they are decomposing under the conditions of the reaction) and can generate undesired by-products during the reaction and afterwards during recovery of the product, e.g., by elevated temperature distillation of the product away from the catalyst residue than phosphonium compounds. The decomposition by-products can be difficult to separate by distillation because of similarity of boiling point and because they are being continually generated during attempts at purification.

Phase transfer catalyzed reaction of a dimetal dicarboxylate with a haloorganoalkoxysilane with use of phosphonium salts such as $Ph_3PMeCl$ suffers from the drawback that the phosphonium salts used are more toxic than their ammonium counterparts.

A thermally stable, amine based phase transfer catalyst, hexaethylguanidinium chloride has also been disclosed. However, hexaethylguanidinium chloride is available as an aqueous solution that must be thoroughly dried before use, which is an undesirable additional, and energy consuming, process step. Hexaethylguanidinium chloride also suffers from the drawback of being difficult to obtain in commercial quantities.

There is a continuing need in the art to provide alternative phase transfer catalysts. Phase transfer catalysts suitable for use in nonaqueous environments are desired.

BRIEF SUMMARY OF THE INVENTION

A method for preparing a reaction product comprising a bis(alkoxysilylorgano)dicarboxylate comprises: reacting a composition comprising:
a) a haloorganoalkoxysilane,
b) a dimetal salt of a dicarboxyl functional compound, and
c) a phase transfer catalyst.

DETAILED DESCRIPTION OF THE INVENTION

Definitions and Usage of Terms

All amounts, ratios, and percentages are by weight unless otherwise indicated. The articles 'a', 'an', and 'the' each refer to one or more, unless otherwise indicated by the context of specification. The prefix "poly" means more than one. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an aryl group, an aralkyl group, or an alkaryl group includes the member alkyl individually; the subgroup alkyl and aryl; and any other individual member and subgroup subsumed therein.

"Aralkyl" and "alkaryl" each refer to an alkyl group having a pendant and/or terminal aryl group or an aryl group having a pendant alkyl group. Exemplary aralkyl groups include benzyl, phenylethyl, phenyl propyl, and phenyl butyl.

"Carbocycle" and "carbocyclic" refer to a hydrocarbon ring. Carbocycles may be monocyclic or alternatively may be fused, bridged, or spiro polycyclic rings. Monocyclic carbocycles may have 3 to 9 carbon atoms, alternatively 4 to 7 carbon atoms, and alternatively 5 to 6 carbon atoms. Polycyclic carbocycles may have 7 to 17 carbon atoms, alternatively 7 to 14 carbon atoms, and alternatively 9 to 10 carbon atoms. Carbocycles may be saturated or partially unsaturated.

"Cycloalkyl" refers to a saturated carbocycle. Cycloalkyl groups are exemplified by cyclobutyl, cyclopentyl, and cyclohexyl.

"Heterocycle" and "heterocyclic" refer to a ring group comprised of carbon atoms and one or more heteroatoms in the ring. The heteroatom may be N, O, P, S, or a combination thereof. Alternatively, the heteroatom may be N. Heterocycles may be monocyclic or alternatively may be fused, bridged, or spiro polycyclic rings. Monocyclic heterocycles may have 3 to 9 member atoms in the ring, alternatively 4 to 7 member atoms, and alternatively 5 to 6 member atoms. Polycyclic heterocycles may have 7 to 17 member atoms, alternatively 7 to 14 member atoms, and alternatively 9 to 11 member atoms. Heterocycles may be saturated or partially unsaturated.

Abbreviations used herein are defined as follows. "GC" means gas chromatography. "NMR" means nuclear magnetic resonance. The abbreviation "ppm" means parts per million. "Et" means ethyl. "Me" means methyl. "Ph" means phenyl. "Pr" means propyl and includes various structures such as iPr and nPr. "iPr" means isopropyl. "nPr" means normal propyl. "Bu" means butyl and includes various structures including nBu, sec-butyl, tBu, and iBu. "iBu" means isobutyl. "nBu" means normal butyl. "tBu" means tertiary-butyl. "Vi" means vinyl.

The method for preparing the bis(alkoxysilylorgano)dicarboxylate will be exemplified with respect to bistalkoxysilylalkyl)fumarates in the description below. However, one skilled in the art would recognize that other bis(alkoxysilylorgano)dicarboxylate compounds (e.g., maleates, itaconates, citraconates, mesaconates, and malonates) may be prepared by varying appropriate starting materials.

Method of Preparing a
Bis(alkoxysilylorgano)Dicarboxylate

A method for preparing a reaction product comprising a bis(alkoxysilylorgano)dicarboxylate comprises: 1) reacting a composition comprising:
  a) a haloorganoalkoxysilane,
  b) a dimetal salt of a dicarboxyl functional compound, and
  c) a phase transfer catalyst.

When ingredient a) is a haloalkylalkoxysilane, and ingredient b) is a dimetal salt of a fumarate, the reaction product comprises a bis(alkoxysilylalkyl)fumarate. A reaction occurs in step 1) to form a reaction product comprising the bis(alkoxysilylorgano)dicarboxylate (e.g., the bis(alkoxysilylalkyl)fumarate) and a metal halide. The composition may optionally further comprise one or more additional ingredients. The additional ingredient is exemplified by, but not limited to, d) a co-catalyst, e) a solvent, f) a stabilizer, and a combination thereof. The method may further comprise step 2) removing at least a portion of the metal halide. The method may further comprise step 3) recovering the bis(alkoxysilylorgano)dicarboxylate, e.g., the bis(alkoxysilylalkyl)fumarate.

Step 1) Reaction Conditions

The reaction in step 1) may be performed by heating the composition at a reaction temperature up to 180° C. for a reaction time up to 18 hours. Alternatively, the reaction temperature may be up to 140° C. Alternatively, the reaction temperature may be up to 120° C. Alternatively, the reaction temperature may range from ambient to 180° C. Alternatively, the reaction temperature may range from 60° C. to 180° C. Alternatively, the reaction temperature may range from 130° C. to 180° C. Alternatively, the reaction temperature may range from 80° C. to 120° C. Alternatively, the reaction time may range from 30 min to 24 hours (h), alternatively 6 h to 18 h, alternatively 6 h to 12 h, alternatively 7 h to 11 h, and alternatively 14 h to 18 h.

The reaction may be performed under substantially anhydrous conditions. Substantially anhydrous conditions means that water content of the composition may range from 0% to 1%, alternatively 0.15% to 0.5%, and alternatively 0.2% to 0.4%, based on the combined weight of the haloorganoalkoxysilane of ingredient a), the dimetal salt of the dicarboxyl functional compound of ingredient b), and the phase transfer catalyst of ingredient c). The absence of water may be accomplished by removing traces of water from the ingredients in the composition. For example, the ingredients may be dried through the aid of a drying agent, such as molecular sieves. The method for preparing the bis(alkoxysilylorgano)dicarboxylate may optionally further comprise: drying one or more of the ingredients before step 1). For example, this step may comprise drying ingredient b) and/or ingredient c) to reduce water content to a level of 1% or less, alternatively 0.05% or less, and alternatively 0.025% or less, in the ingredient before heating in step 1).

The reaction may be performed under substantially inert conditions. For example, step 1) may be performed under an inert gas blanket, such as a nitrogen blanket.

Ingredient a) Haloorganoalkoxysilane

The haloorganoalkoxysilane of ingredient a) used in the method described herein may have formula (I): $X_a R^2_b Si(OR^1)_{(4-a-b)}$, where subscript a is 1 or 2, alternatively 1; and subscript b is 0, 1, or 2; alternatively 0 or 1; alternatively 1; and alternatively 0; with the proviso that a quantity (a+b)<4. Each X is independently a halogenated organic group. Group X may be an alkyl group which contains at least one halogen atom such as Cl, Br, or I; alternatively Cl. Exemplary groups for X include chloromethyl, chloropropyl, bromopropyl, iodopropyl or chloroisobutyl. Alternatively, X may be selected from chloromethyl and chloropropyl.

In formula (I), each $R^1$ is independently a hydrocarbyl group. The hydrocarbyl groups represented by $R^1$ typically have 1 to 6 carbon atoms, alternatively 1 to 4 carbon atoms. Acyclic hydrocarbyl groups containing at least three carbon atoms can have a branched or unbranched structure. Examples of hydrocarbyl groups for $R^1$ include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl.

In formula (I), each $R^2$ is independently a hydrocarbyl group. The hydrocarbyl groups represented by $R^2$ typically have 1 to 10 carbon atoms, alternatively 1 to 6 carbon atoms, and alternatively 1 to 4 carbon atoms. Acyclic hydrocarbyl groups containing at least three carbon atoms can have a branched or unbranched structure. Examples of hydrocarbyl groups include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as methylcyclohexyl, cyclopentyl and cyclohexyl; aryl, such as phenyl and naphthyl; aralkyl such as tolyl, xylyl, benzyl, and phenylethyl, and aralkenyl such as styryl and cinnamyl; alkenyl, such as vinyl, allyl, propenyl, and hexenyl; and alkynyl, such as ethynyl and propynyl.

Examples of the haloorganoalkoxysilane of formula (I) include, but are not limited to, chloromethyldimethylmethoxysilane, chloromethyltrimethoxysilane, chloromethyltriethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, 3-chloropropylethyldimethoxysilane, 3-chloropropylethyldiethoxysilane, 3-bromopropyltrimethoxysilane, 3-bromopropyltriethoxysilane, 3-iodopropyltrimethoxysilane, 3-iodopropyltriethoxysilane, chlorobutylphenylmethyl-n-propoxysilane, chloromethyldimethylmethoxysilane, 3-chloro-2-methylpropyltrimethoxysilane or chloromethyltrimethoxysilane. Alternatively, the haloorganoalkoxysilane of formula (I) is 3-chloropropyltrimethoxysilane or 3-chloropropyltriethoxysilane.

The amount of haloorganoalkoxysilane for ingredient a) may range from 1% to 99%, based on the combined weights of ingredients a) and b). Alternatively, the amounts of ingredient a) and ingredient b) may be selected to provide a 2:1 molar ratio of haloorganoalkoxysilane and dimetal salt of a dicarboxylate.

Ingredient b) Dimetal Salt of Dicarboxyl Functional Compound

Ingredient b) used in the method described above is the dimetal salt of the dicarboxyl-functional compound. Ingredient b) may have formula (II):

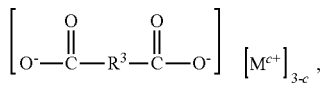

where $M^+$ is a cation selected from an alkali metal cation or alkaline earth metal cation or an ammonium cation; c is 1 or 2, alternatively 1; and $R^3$ is a divalent organic group. Examples of alkali metal or alkaline earth metal cations represented by $M^+$ include $Li^+$, $Na^+$, $K^+$, $Mg^{2+}$, and $Ca^{2+}$; tetramethylammonium, tetraethylammonium, trimethylammonium, and triethylammonium. Alternatively, $M^+$ is $Na^+$ or $K^+$. $R^3$ may be $CH_2$, $C_2H_2$, $C_2H_4$, or $C_3H_4$. Examples of ingredient b) include, but are not limited to, disodium fumarate, disodium maleate, disodium itaconate, dipotassium fumarate, dipotassium maleate, and dipotassium itaconate.

Alternatively, when ingredient b) is the dimetal salt of the fumarate, ingredient b) may have formula (IIa):

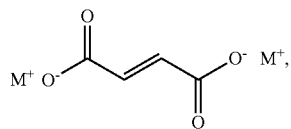

where each M+ is as described above. Ingredient b) may be dipotassium fumarate or disodium fumarate. The amount of the dimetal salt of the fumarate of formula (IIa) may range from 1% to 50% based on the combined weights of ingredients a) and b). Alternatively, the amounts of ingredient a) of formula (I) and ingredient b) of formula (IIa) may be selected to provide a 2:1 molar ratio of ingredient a): ingredient b).

Ingredient c) Phase Transfer Catalyst

The phase transfer catalyst of ingredient c) comprises a bicyclic amidine, a quaternary iminium compound of the bicyclic amidine, or a combination thereof. Ingredient c) may comprise a polyaza, polycycloalkene, such as a polyazabicycloalkene. Alternatively, ingredient c) may comprise a polyaza, polycycloalkene quat, such as a polyazabicycloalkene quat. Suitable polyazabicycloalkenes, and salts thereof; and methods for their preparation are disclosed, for example, in U.S. Pat. Nos. 3,769,244; 4,524,104; 4,465,867; and 4,465,868. Alternatively, the phase transfer catalyst of ingredient c) may comprise a diazabicycloalkene such as those disclosed in U.S. Pat. Nos. 3,769,244 and 4,524,104 at col. 2, at lines 31-54. Examples of diazabicycloalkenes include, but are not limited to, i) 1,5-diazabicyclo[4.2.0]oct-5-ene;
ii) 1,8-diazabicyclo[7.2.0]undec-8-ene;
iii) 1,4-diazabicyclo[3.3.0]oct-4-ene;
iv) 3-methyl-1,4-diazabicyclo[3.3.0]oct-4-ene;
v) 3,6,7,7-tetramethyl-1,4-diazabicyclo[3.3.0]oct-4-ene;
vi) 7,8,8-trimethyl-1,5-diazabicyclo[4.3.0]non-5-ene;
vii) 1,8-diazabicyclo[7.3.0]tridec-8-ene;
viii) 1,7-diazabicyclo[4.3.0]non-6-ene;
ix) 1,5-diazabicyclo[4.4.0]dec-5-ene;
x) 1,5-diazabicyclo[4.3.0]non-5-ene (DBN);
xi) 1,8-diazabicyclo[7.4.0]tridec-8-ene;
xii) 1,8-diazabicyclo[7.3.0]dodec-8-ene;
xiii) 1,8-diazabicyclo[5.3.0]dec-7-ene;
xiv) 9-methyl-1,8-diazabicyclo[5.3.0]dec-7-ene;
xv) 9-methyl-1,8-diazabicyclo[5.4.0]undec-7-ene;
xvi) 1,8-diazabicyclo[5.4.0]undec-7-ene (DBU);
xvii) 1,6-diazabicyclo[5.5.0]dodec-6-ene;
xviii) 1,7-diazabicyclo[6.5.0]tridec-7-ene;
xix) 1,8-diazabicyclo[7.5.0]tetradec-8-ene;
xx) 1,10-diazabicyclo[7.3.0]dodec-9-ene;
xxi) 1,10-diazabicyclo[7.4.0]tridec-9-ene;
xxii) 1,14-diazabicyclo[11.3.0]hexadec-13-ene;
xxiii) 1,14-diazabicyclo[11.4.0]heptadec-13-ene;
xxiv) 1,8-diazabicyclo[5.3.0]dec-7-ene; and
xxv) combinations thereof.

Alternatively, the polyaza, polycycloalkene may comprise a triazabicycloalkene, such as 1,5,7-triazabicyclo[4.4.0]dec-5-ene or 7-methyl-1,5,7-triazabicyclo[4.4.0]dec-5-ene (MTBD), both of which are commercially available from Sigma-Aldrich, Inc. of St. Louis, Mo., U.S.A.

Alternatively, the polyaza, polycycloalkene may be a polyazabicycloalkene selected from the group consisting of DBU, DBN, MTBD, or a combination thereof. Alternatively, the polyazabicycloalkene may be selected from the group consisting of DBN and MTBD, see structures below.

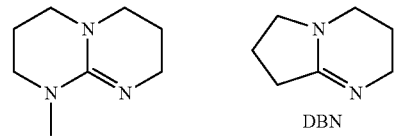

MTBD      DBN

The polyaza, polycycloalkene may have general formula (IV):

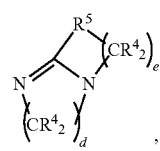

where
each $R^4$ is independently a hydrogen atom or a monovalent hydrocarbyl group,
$R^5$ is a divalent organic group, and
subscript d is an integer with a value of at least 2, and
subscript e is an integer with a value of at least 1.

The hydrocarbyl groups represented by $R^4$ may have 1 to 18 carbon atoms, alternatively 1 to 12 carbon atoms, alternatively 1 to 6 carbon atoms, and alternatively 1 to 4 carbon atoms. Acyclic hydrocarbyl groups containing at least three carbon atoms can have a branched or unbranched structure. Examples of hydrocarbyl groups for $R^4$ include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl. Alternatively, each $R^4$ may be a hydrogen atom or an alkyl group of 1 to 4 carbon atoms. Alternatively, each $R^4$ may be a hydrogen atom.

In formula (IV), the divalent organic groups for $R^5$ may be alkylene groups such as $(CR^4{}_2)_d$, where $R^4$ and subscript d are as defined above. Alternatively, the divalent organic group for $R^5$ may contain a heteroatom. The divalent organic group for $R^5$ may have formula: $R^8N(CR^4{}_2)_d$ where $R^4$ and subscript d are as defined above and $R^8$ is a hydrogen atom or a hydrocarbyl group that may have 1 to 6 carbon atoms, alternatively 1 to 4 carbon atoms. Examples of hydrocarbyl groups for $R^8$ include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl. Alternatively, each $R^8$ may be a hydrogen atom or Me. Alternatively in formula (IV), subscript d may be an integer with a value ranging from 2 to 6, alternatively 2 to 4. Alternatively, subscript d may be an integer with a value ranging from 2 to 6, alternatively 2 to 4.

The quaternary iminium compound of the bicyclic amidine may be prepared by the methods described below in the examples. For example, a polyaza, polycycloalkene quat may be prepared by a method comprising: reacting ingredients comprising i) the polyaza, polycycloalkene described above and ii) an organofunctional compound of formula (V): $R^6R^7$, where each $R^6$ is an alkyl group or an aralkyl group, and each $R^7$ is a counter ion that is a halogen. Each $R^7$ may be independently selected from the group consisting of $Cl^-$, $Br^-$, and $I^-$; alternatively $Cl^-$ or $Br^-$; alternatively $Cl^-$; and alternatively $Br^-$. The method may include heating the ingredients, for example, to a temperature ranging from 50° C. to 180° C. The organofunctional compound of formula (V) may be an alkyl halide such as an n-alkyl halide. Suitable alkyl halides include, but are not limited to, 2-ethylhexyl bromide, 1-bromooctane, 1-chlorooctane, 1-bromobutane, 1-bromododecane, 2-ethylhexyl chloride, 1-chlorobutane, and 1-chlorododecane. Alternatively, the alkyl halide may be selected from the group consisting of the bromine compounds listed above. Alternatively, the alkyl halide may be selected from the group consisting of the chlorine compounds listed above. Alternatively, the n-alkyl halide may be selected from the group consisting of the n-alkyl bromides listed above. Alternatively, the n-alkyl halide may be selected from the group consisting of the n-alkyl chlorides listed above.

Alternatively in formula (V), $R^6$ is an n-alkyl group of 1 to 12 carbon atoms, and $R^7$ is a halogen counter ion selected from Cl and Br. Alternatively, $R^6$ is an n-alkyl group of 1 to 12 carbon atoms, and $R^7$ is Cl. Alternatively, $R^6$ is an n-alkyl group of 1 to 12 carbon atoms, and $R^7$ is Br. The resulting reaction product comprises a polyaza, polycycloalkene quat and a polyaza, polycycloalkene salt byproduct; and this reaction product may be used as the phase transfer catalyst of ingredient c) in the method described above.

Model Reaction for Preparing Polyaza, Polycycloalkene Quats

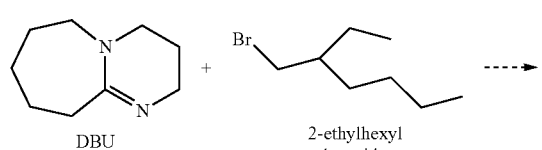

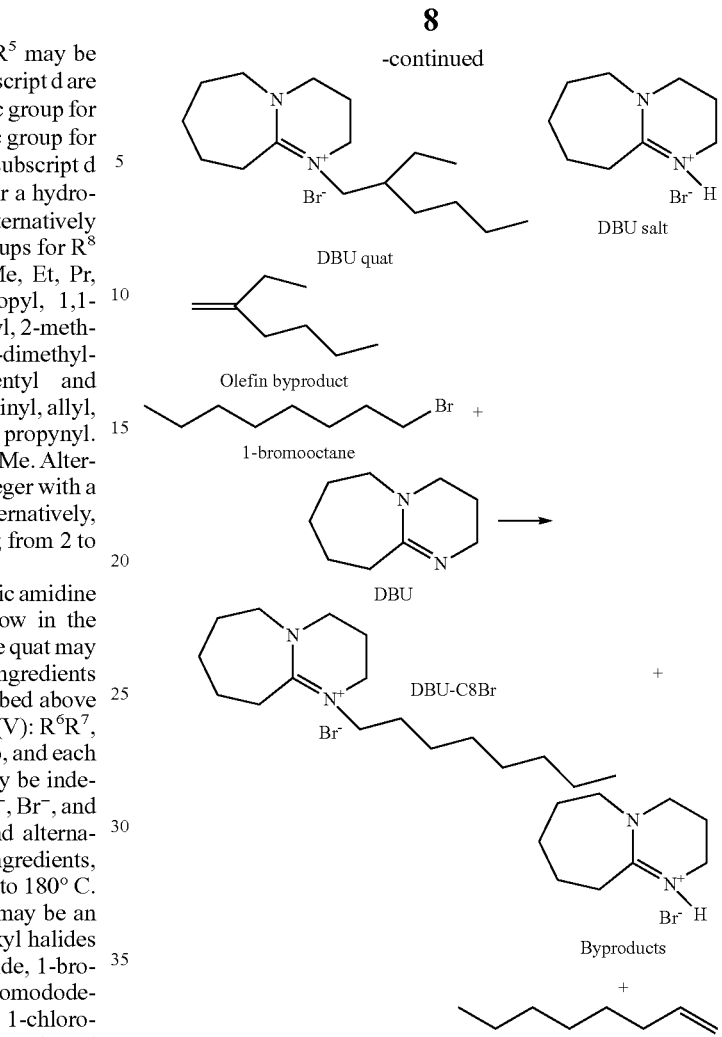

Alternatively, the method for preparing the reaction product comprising the polyaza, polycycloalkene quat described above may optionally further comprise purification of the polyaza, polycycloalkene quat. Suitable purification methods are known in the art, for example, see "Synthesis and crystal structure of new phase-transfer catalysts based on 1,8-diazabicyclo[5.4.0]undec-7-ene and 1,5-diazabicyclo[4.3.0]non-5-ene", Progr. Colloid Polym. Sci. (2004) 123: 28-30). The polyaza, polycycloalkene quat (free of by-product(s) such as the salt and/or the olefin) may be used as the phase transfer catalyst of ingredient c) in the method described above.

Alternatively, the quaternary iminium compound of the bicyclic amidine (bicyclic amidine quat) may be prepared by ion exchange, for example, when i) the polyaza, polycycloalkene described above is reacted with ii) an organofunctional compound of formula (V): $R^6R^7$, where $R^6$ is as described above, and each $R^7$ halide counter ion described above can be exchanged with a counter ion selected from the group consisting of $HSO_4^-$, $HCO_3^-$, acetate, $SO_4^{2-}$, $CO_3^{2-}$, $HPO_4^{2-}$, and $PO_4^{3-}$. Alternatively, the bicyclic amidine quat may be commercially available. For example, benzyl-1,8-diazabicyclo[5.4.0]undec-7-enium chloride (benzyl-DBU chloride) is commercially available from Akzo Nobel of Norcross, Ga., U.S.A.

Other exemplary quaternary iminium compounds of bicyclic amidines suitable for ingredient c) include, but are not limited to, halides, acetates, sulfates, phosphates, and carbonates of the exemplary diazabicycloalkenes designated i) to xxiv) above (in paragraph [0027]). Alternatively, the quaternary iminium compound of the bicyclic amidine may be selected from the group consisting of:
i) 5-octyl-1,5-diazabicyclo-[4.2.0]oct-5-enium halide (e.g., bromide or chloride);
ii) 8-undecyl-1,8-diazabicyclo-[7.2.0]undec-8-enium halide;
iii) 4-octyl-1,4-diazabicyclo-[3.3.0]oct-4-enium halide;
iv) 3-methyl-4-octyl-1,4-diazabicyclo[3.3.0]oct-4-enium halide;
v) 3,6,7,7-tetramethyl-4-octyl-1,4-diazabicyclo[3.3.0]oct-4-enium halide;
vi) 5-octyl-7,8,8-trimethyl-1,5-diazabicyclo[4.3.0]non-5-enium halide;
vii) 8-tridecyl-1,8-diazabicyclo[7.3.0]dodec-8-enium halide;
viii) 7-nonyl-1,7-diazabicyclo[4.3.0]non-6-enium halide;
ix) 5-decyl-1,5-diazabicyclo[4.4.0]dec-5-enium halide;
x) 5-nonyl-1,5-diazabicyclo[4.3.0]non-5-enium halide;
xi) 8-tridecyl-1,8-diazabicyclo[7.4.0]tridec-8-enium halide;
xii) 8-dodecyl-1,8-diazabicyclo[7.3.0]dodec-8-enium halide;
xiii) 8-decyl-1,8-diazabicyclo[5.3.0]dec-7-enium halide;
xiv) 8-decyl-9-methyl-1,8-diazabicyclo[5.3.0]dec-7-enim halide;
xv) 8-undecyl-9-methyl-1,8-diazabicyclo[5.4.0]undec-7-enium halide;
xvi) 8-undecyl-1,8-diazabicyclo[5.4.0]undec-7-enium halide;
xvii) 6-octyl-1,6-diazabicyclo[5.5.0]dodec-6-enium halide;
xviii) 7-tridecyl-1,7-diazabicyclo[6.5.0]tridec-7-enium halide;
xix) 8-tetradecyl-1,8-diazabicyclo[7.5.0]tetradec-8-enium halide;
xx) 10-dodecyl-1,10-diazabicyclo[7.3.0]dodec-9-enium halide;
xxi) 10-tridecyl-1,10-diazabicyclo[7.4.0]tridec-9-enium halide;
xxii) 14-hexadecyl-1,14-diazabicyclo[11.3.0]hexadec-13-enium halide;
xxiii) 14-hapetadecyl-1,14-diazabicyclo[11.4.0]heptadec-13-enium halide;
xxiv) 8-decyl-1,8-diazabicyclo[5.3.0]dec-7-enium halide; and
xxv) combinations thereof.

Alternatively, the quaternary iminium compound of the bicyclic amidine (bicyclic amidine quat) may be a polyazabicycloalkene quat. The polyazabicycloalkene quat may have formula (VI):

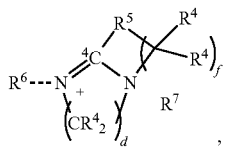

where $R^4$, $R^5$, $R^6$, $R^7$, and subscripts d and e are as described above.

Alternatively, the phase transfer catalyst of ingredient c) may be selected from the group consisting of: DBU, a DBU-alkyl halide quat, or a combination thereof.

The amount of the phase transfer catalyst added to the composition as ingredient c) depends on various factors including the types and amounts selected for ingredients a) and b), whether any additional ingredients, such as d) a co-catalyst, e) a solvent, f) a stabilizer, or a combination thereof, are added to the composition. However, the amount of the phase transfer catalyst added to the composition as ingredient c) may range from 0.1 mol % to 20 mol %, and alternatively 1 mol % to 10 mol %. Alternatively, the amount of phase transfer catalyst may range from 0.01 mol % to 15 mol %, alternatively 0.1 mol % to 10 mol %, alternatively 0.1 mol % to 7.5 mol %, and alternatively 2.5 mol % to 5 mol %.

Ingredient d) Co-Catalyst

Ingredient d), a co-catalyst, may optionally be used in the method for making a bis(alkoxysilylorgano)dicarboxylate described herein. The co-catalyst is selected based on various factors including the type of phase transfer catalyst selected for ingredient c). The co-catalyst has higher solubility than the PTC selected as ingredient c). Without wishing to be bound by theory, it is thought that the co-catalyst may increase the reaction rate for forming the bis(alkoxysilylorgano)dicarboxylate as compared to the reaction rate achievable using the same reaction conditions and the same ingredients except for omitting the co-catalyst. Without wishing to be bound by theory, it is thought that adding, as ingredient d), a salt bearing an anion of lower lipophilicity than the phase transfer catalyst of ingredient c) may provide the benefit of increasing reaction speed. It is further believed that in accordance to the theory of hard and soft acids and bases these harder anions demonstrate a lower affinity to the onium cation of the phase transfer catalyst in competition with the anion of the phase transfer catalyst, the nucleophile and the leaving group of the haloorgano group on ingredient a) while increasing the ionic strength of the composition. The amount of the co-catalyst may range from 0 mol % to 100% of the molar amount of the phase transfer catalyst of ingredient c). The co-catalyst of ingredient d) may be combined with ingredient c) or with ingredient b) before step 1) of the method described herein. Alternatively, ingredient d) may be added to the composition during step 1).

Exemplary co-catalysts for ingredient d) comprise metal compounds of formula $M^+R^9$, where $M^+$ is as described above and $R^9$ is selected from the group consisting of $HSO_4^-$, $HCO_3^-$, acetate, $SO_4^{2-}$, $CO_3^{2-}$ and $PO_4^{3-}$. Exemplary co-catalysts for ingredient d) include metal acetates, such as potassium acetate and/or sodium acetate; metal sulfates such as $K_2SO_4$ and/or $Na_2SO_4$; metal hydrogen sulfates such as $KHSO_4$ and/or $NaHSO_4$; metal carbonates such as $K_2CO_3$ and/or $Na_2CO_3$; metal hydrogen carbonates such as $KHCO_3$ and/or $NaHCO_3$; or metal phosphates such as $K_2HPO_4$, $K_3PO_4$ and/or $Na_3PO_4$.

Ingredient e) Solvent

Ingredient e), a solvent, may optionally be used in the method for making a bis(alkoxysilylorgano)dicarboxylate described herein. The solvent for ingredient e) may be combined with one or more of the ingredients described above before step 1) of the method described herein. Alternatively, the solvent may be added during step 1). The solvent may be a polar aprotic solvent, such as dimethyl formamide (DMF), n-methylpyrrolidone (NMP), dimethyl sulfoxide (DMSO), or a combination thereof. The amount of solvent for ingredient d) may range from 10% to 200% based on the combined weight of all ingredients in the composition.

Alternatively, the reaction in step 1) may be performed neat, i.e., without adding a solvent. Without wishing to be bound by theory, it is thought that ingredient a) and/or the product (e.g., bis(alkoxysilylalkyl)fumrate) may solubilize ingredients a), b) and/or c) in the composition to facilitate the reaction in the absence of an additional solvent.

Ingredient f) Stabilizer

Ingredient f), a stabilizer, may optionally be used in the method for making a bis(alkoxysilylorgano)dicarboxylate described herein. The stabilizer for ingredient f) may be combined with one or more of the ingredients described above before step 1) of the method described herein. Alternatively, the solvent may be added during step 1). The stabilizer for ingredient f) may be a stabilizer commonly used with acrylates, such as butylated hydroxytoluene (BHT), phenothiazine (PTZ), hydroquinone and derivatives thereof such as monomethyl ether of hydroquinone (MEHQ), and combinations thereof. Suitable stabilizers, such as those listed above are commercially available from Sigma-Aldrich, Inc. of St. Louis, Mo., U.S.A. The amount of stabilizer may range from 0 to 1,500 ppmw. Alternatively, the amount of stabilizer, when present, may range from 10 ppmw to 1,000 ppmw based on the combined weight of all ingredients in the composition.

The reaction in step 1) of the method described above forms a reaction product comprising the bis(alkoxysilylorgano)dicarboxylate, such as the bis(alkoxysilylalkyl)fumarate, as described above. The reaction product further comprises a first metal halide having formula (III): $M^{x-}+X^-_x$, where $X^-$ is a halide anion, M is a metal atom, and x is the valence of M.

Step 2) Removing Metal Halide in the First Embodiment

The method described above may further comprise step 2): removing at least a portion of the first metal halide from the reaction product. As used herein, "a portion" means enough to reduce the metal halide in the reaction product to within the ranges described below. For example, a portion is typically at least 50%, alternatively at least 90%, alternatively at least 99.99%, of the initial amount of the metal halide in the reaction product.

The metal halide may be removed from the reaction product by processes known in the art for removing a solid metal halide from an organic material. The metal halide may be removed by, for example, filtering, centrifuging, decanting, washing, or a combination thereof. For example, the metal halide may be removed by filtration or decantation. Alternatively, the metal halide may be removed by decanting the bis(alkoxysilylalkyl)fumarate from the metal halide followed by washing with a solution, as described below.

After removing at least a portion of the metal halide from the reaction product, the bis(alkoxysilylorgano)dicarboxylate typically contains the metal halide in an amount less than 10,000 parts per million by weight (ppmw), alternatively 1 ppmw to 1,000 ppmw, alternatively 10 ppmw to 100 ppmw, based on the weight of the bis(alkoxysilylorgano)dicarboxylate of the first metal halide.

Step 2) Removing Metal Halide in the Second Embodiment

Alternatively, removing at least a portion of the metal halide in step 2) may be performed by a method comprising washing a mixture comprising i) the reaction product formed in step 1) (i.e., the reaction product comprising the bis(alkoxysilylorgano)dicarboxylate and the metal halide of formula (III)), and ii) a non-polar solvent with a solution comprising i) water and, optionally, ii) a second metal halide, to produce an organic phase comprising the bis(alkoxysilylalkyl)fumarate and an aqueous phase comprising at least a portion of the first metal halide (i.e., the metal halide of formula (III) formed by the reaction in step 1)).

The non-polar solvent has a dielectric constant below 10, alternatively below 5, alternatively from 1 to 5. The non-polar solvent has a density less than 1.0 grams per milliliter (g/mL), alternatively from 0.6 to 0.9 grams per mL, alternatively from 0.7 to 0.8 g/mL, at 25° C. Examples of the non-polar solvents include, but are not limited to, organic solvents such as mineral spirits, toluene, m-, o-, and p-xylene and mixtures thereof, n-pentane, n-hexane, n-heptane, cyclopentane, cyclohexane, cyclooctane, cyclohexane, cis-cyclooctene, tert-butyl methyl ether and di-n-butyl ether.

The mixture may be formed by adding the non-polar solvent to the composition in step 1). Alternatively, the mixture may be formed by combining the non-polar solvent with the reaction product comprising the bis(alkoxysilylalkyl)fumarate and the first metal halide in the reactor and with the conditions typically used for blending solutions. For example, the combining may be done at ambient temperatures in a mixing tank with a mixing blade.

The bis(alkoxysilylalkyl)fumarate is typically present in the mixture at an amount ranging from 1% to 90%, alternatively from 10% to 80%, alternatively from 30% to 70%, based upon the combined weight of the non-polar solvent, the bis(alkoxysilylalkyl)fumarate, and the first metal halide.

The non-polar solvent is present in the mixture at an amount ranging from 10% to 90%, alternatively 15% to 80%, alternatively 25% to 60%, based on the combined weight of the non-polar solvent, the bis(alkoxysilylalkyl)fumarate, and the first metal halide.

The first metal halide is typically present in the mixture at an amount ranging from 1% to 50%, alternatively 5% to 30%, alternatively 5% to 15%, based on the combined weight of the bis(alkoxysilylalkyl)fumarate, the non-polar solvent, and the first metal halide. The amount of the first metal halide in the mixture may be calculated stoichiometrically or determined by processes known in the art for determining the amount of a metal halide in a mixture, for example by ion chromatography.

The solution comprises i) water and, optionally, ii) a second metal halide. For example, the solution may comprise an amount ranging from 0% to a less than a saturated concentration, alternatively from 0% to 50%, alternatively from 0% to 15%, based on the combined weight of the second metal halide and the water, of the second metal halide. As used herein, a "saturated concentration" means the concentration, at a particular temperature and pressure, at which no additional amount of the second metal halide will dissolve. The water is typically deionized water; however, other types of water, such as distilled water or tap water, may be used.

The second metal halide is as described and exemplified above for the first metal halide of formula (III). The second metal halide may be the same or different as the first metal halide and may be a mixture of metal halides, each according to the formula (III) herein. In one embodiment, the second metal halide is the same as the first metal halide and is potassium chloride or sodium chloride. Alternatively, the second metal halide may be replaced with a salt that does not react, or that does not induce reactions, can be used in place of the second metal halide. Examples of such salts include carbonates.

Examples of solutions useful in the second process of the invention include water and less than saturated aqueous solutions of sodium chloride, sodium bromide, potassium chloride, or potassium bromide. When the solution comprises the second metal halide, the solution may be made by processes known in the art for making such solutions. Many aqueous solutions of metal halides are available commercially.

Step 2) in this embodiment may be conducted in any vessel known in the art for washing an organic solution with water. For example, step 2) may be conducted in a stainless steel tank equipped with mechanical mixing. The time required for step 2) in this embodiment is equal to the time required to combine and mix the solution and the mixture and for the solution to extract the first metal halide from the mixture. For example, the time of required for step 2) in this embodiment may range from 1 minute (min) to 60 min, alternatively 5 min to 45 min, alternatively 10 min to 45 min.

The order and rate of addition of the solution in this embodiment is generally not critical. Typically the solution and mixture may be added at any rate and in any order.

The temperature at which step 2) in this embodiment is conducted may range from 0° C. to 120° C., alternatively from 0° C. to 60° C., and alternatively from 10° C. to 40° C.

The pressure at which step 2) in this embodiment is conducted may range from sub-atmospheric to super-atmospheric pressures, alternatively 0 to 1000 kPag, alternatively from 0 to 100 kPag, and alternatively pressure at which step 2) in this embodiment is conducted may be atmospheric pressure.

In this embodiment, the mixture is washed with a sufficient amount of the solution so the first metal halide and the second metal halide together are at least 15%, alternatively at least 18%, and alternatively 18% to 50%, of the combined weight of the first metal halide, the second metal halide, and the water. As used herein, a "sufficient amount" is an amount that is not too great to cause the combined percentage of the first metal halide and the second metal halide to be outside the prescribed limits A sufficient amount of the solution may be calculated from the weight of the first metal halide in the mixture and the second metal halide and water in the solution, which may be determined using processes known in the art, for example by ion chromatography.

The washing produces an organic phase, comprising the bis(alkoxysilylorgano)dicarboxylate and the non-polar solvent, and an aqueous phase, comprising the solution and at least a portion of the first metal halide. The organic and aqueous phases are immiscible.

The aqueous phase comprises at least 15%, alternatively at least 18%, alternatively from 18% to a saturated concentration, based on the weight of the first metal halide, the second metal halide, and the water, of the first metal halide and second metal halide combined. After washing in step 2) in this embodiment, the bis(alkoxysilylorgano)dicarboxylate may comprise less than 10,000 ppmw, alternatively 1 ppmw to 1000 ppmw, alternatively 10 ppmw to 100 ppmw, based on the weight of the bis(alkoxysilylorgano)dicarboxylate, of the first metal halide.

This embodiment provides relatively fast separation of the bis(alkoxysilylorgano)dicarboxylate and metal halide (i.e., faster than filtration). Further, this embodiment eliminates the need for the filtration of the organic phase. Still further, this embodiment allows for washing the bis(alkoxysilylorgano) dicarboxylate without significant hydrolysis and without formation of a dispersion that is difficult to separate.

Alternatively, when an optional polar aprotic solvent for ingredient d) is used in step 1) of the method described herein, the polar aprotic solvent is removed from the reaction product before adding the non-polar solvent. The polar aprotic solvent of ingredient d) can be removed by any convenient means, such as stripping or distillation under atmospheric or reduced pressure.

Step 3) Recovering the Bis(alkoxysilylalkyl)Fumarate

The method may optionally further comprise step 3): recovering the bis(alkoxysilylorgano)dicarboxylate. Step 3) may be performed during or after step 2) of the method described above. Recovering may be accomplished by processes known in the art. For example, recovering may be performed by a method comprising stripping or distillation at elevated temperature and/or reduced pressure. When the second embodiment is performed for step 2), the organic phase and the aqueous phase may be separated using known processes, such as by decantation, followed by distillation of the organic phase.

Methods of Use

The bis(alkoxysilylorgano)dicarboxylate, particularly the bis(alkoxysilylalkyl)fumarate, prepared by the method described herein may be used as a coupling agent for unsaturated resin or polymer systems, an adhesion promoter at organic-inorganic interfaces, and as a surface modifier.

The bis(alkoxysilylorgano)dicarboxylate, e.g., the bis (alkoxysilylalkyl)fumarate, and particularly, bis(triethoxysilylpropyl)fumarate, prepared by the method described herein is particularly useful in engineered rubber goods applications. Such applications include belts and/or hoses. Alternatively, the bis(alkoxysilylorgano)dicarboxylate, e.g., the bis (alkoxysilylalkyl)fumarate, and particularly, bis (triethoxysilylpropyl)fumarate, prepared by the method described herein is particularly useful in tire applications, such as in a rubber composition used for preparing a tire, or a portion thereof, e.g., a tread. The rubber composition may be suitable for use in tires for various applications, e.g., race cars, heavy-vehicle applications such subway trains and buses, for tires for vehicles transporting heavy loads, construction vehicles, agricultural vehicles, 4×4 vehicles, passenger vehicles, vans, sport utility vehicles, aircraft, and/or motor vehicles. The rubber composition may be used in the manufacture of new tires and/or for re-treading worn tires. An exemplary such rubber composition typically comprises A) a diene polymer such as a polyisoprene, a polybutadiene, a polyvinylaromatic polymer, or a natural rubber, B) a reinforcing filler such as silica and/or carbon black and/or natural fibers, e.g., starch and/or cellulose, and C) a bis(alkoxysilylorgano)dicarboxylate such as bis(alkoxysilylalkyl)fumarate, prepared by the method described herein. Alternatively, ingredient C) may comprise bis(triethoxysilylpropyl)fumarate, prepared by the method described herein. The bis(alkoxysilylorgano)dicarboxylate, particularly the bis(alkoxysilylalkyl)fumarate, (e.g., bis(triethoxysilylpropyl)fumarate) prepared by the method described herein may be added to a rubber composition as described in, for example, any one of U.S. Pat. Nos. 5,811,479; 6,071,995; 6,903,155; 6,900,263; 7,078,449; 7,186,776; 7,256,233; 7,300,970; 7,629,408; and 7,718,717; and PCT Publications WO 2010/000478, WO2010/125123, and WO2010/125124; in addition to, or instead of, the alkoxysilane and/or coupling agent in the rubber compositions described therein.

EXAMPLES

These examples are intended to illustrate some embodiments of the invention and should not be interpreted as limiting the scope of the invention set forth in the claims. Reference examples should not be deemed to be prior art unless so indicated. The following ingredients are used in the examples below.

| Raw Material (Abbreviated) | Raw Material Name | Supplier |
|---|---|---|
| DBU | 1,8-Diazabicyclo[5.4.0]undec-7-ene | Aldrich |
| DBU-Octyl Bromine | DBU-octyl bromide (or DBU quat): Quaternary salt of DBU using octyl-bromine | prepared as described in the reference examples herein |
| DBU-Octyl Bromine/Potassium Acetate (KAc) | Potassium acetate and Quaternary salt of DBU using octyl-bromide | Mixture of DBU-Octyl Bromine prepared as above and KAc from Aldrich |
| TBAB | Tetratbutylammonium Bromide | Aldrich |
| TBA-Acetate | Tetrabutylammonium Acetate | Aldrich |
| TBA-Chloride | Tetrabutylammonium Chloride | Aldrich |
| TBA-Hydrogenosulfate | Tetrabutylammonium Hydrogenosulfate | Aldrich |
| TBAB/Potassium Acetate (KAc) | — | Mixture of TBAB and KAc, both from Aldrich |
| KAc | Potassium Acetate | Aldrich |
| CPTES | Chloropropyltriethoxysilane | DCC |
| Disodium Fumarate | — | Aldrich |
| Dipotassium Fumarate | — | MP Biomedicals, LLC. |
| PTZ | Phenothiazine | Aldrich |
| BHT | butylated hydroxytoluene; 2,6-bis(1,1-dimethylethyl)-4-methylphenol | Aldrich |

In the table above, "Aldrich" refers to Sigma-Aldrich, Inc. of St. Louis, Mo., U.S.A. Chloropropyltriethoxysilane was commercially available as DOW CORNING® Z-6376 from Dow Corning Corporation of Midland, Mich., U.S.A.

Reference Examples 1 to 8

General Procedure for Preparation of Quats

Polyazabicycloalkene quats: alkyl halide quats (iminium salts) were prepared by combining a polyazabicycloalkene (described above) and an alkyl halide. The alkyl halides tested were 2-ethylhexyl bromide, 1-bromobutane, 1-bromooctane, 1-bromododecane, and 1-chlorooctane. The combinations were heated in some instances. Synthesis of the resulting iminium salts is illustrated below for DBU+2-ethylhexyl bromide in the model reactions shown below. The competing reaction of elimination, to form an olefin by-product, accounted for 63 mol % of the reaction mixture, leaving 37 mol % DBU:ethylhexyl bromide quat. This reaction product can be used as a phase transfer catalyst for ingredient c) in the method described above without purification. Alternatively, purification of the DBU quat before use of said quat as the phase transfer catalyst of ingredient c) may be performed by any convenient means, as described above in the specification. Replacing the 2-ethylhexyl bromide with 1-bromooctane, as shown in the model reactions, below increased the yield of the resulting DBU:octylbromide quat to 98 mol %. Other n-alkyl halides such as 1-chlorooctane, 1-bromobutane and 1-bromododecane were also reacted with DBU to form the corresponding iminium salt, suitable for use as a phase transfer catalyst.

Model Reactions for Preparing DBU Quats

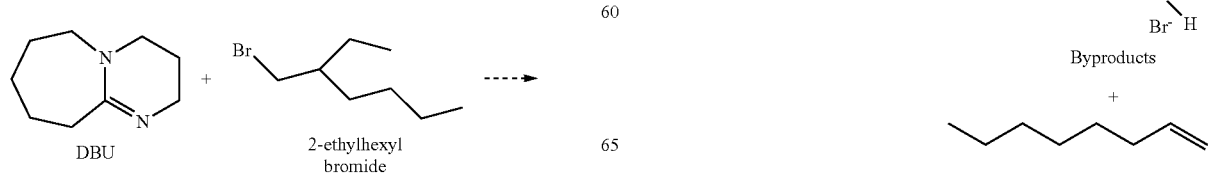

Reference Example 1

DBU 2-Ethylhexyl Bromide Quat

To a 15 ml vial were added 3.03 g (19.9 mmol) of DBU and 3.84 g (19.9 mmol) of 2-ethylhexyl bromide. The vial was vortex mixed to form a clear solution and placed in an oven at 80° C., removed and briefly vortex mixed after 7 minutes then returned to the oven. The contents were hazy after 7 minutes. The vial was removed from the oven after 30 minutes. The contents separated into two phases, a thick lower phase and a thinner upper phase. $^1$H NMR showed the upper phase to be a mixture of starting materials and 2-ethylhexene. By $^1$H NMR, the crude material lower phase was 37 mol % quat salt and the balance was DBU.HBr and a small amount of 2-ethylhexene. The crude material lower phase was evaluated as a phase transfer catalyst without purification. In a separate preparation, the crude product was purified by dissolution in methylene chloride, washing with deionized (DI) water, drying of the organic layer over $MgSO_4$, and addition of pentane to the organic layer to form two phases. The pentane layer, containing mostly 2-ethylhexene, was discarded. The methylene chloride layer was vacuum stripped to 50° C. @ 4 ton to isolate the pure quat salt.

Reference Example 2

MTBD 2-Ethylhexyl Bromide Quat

To a 2 ml vial was added 0.48 g (3.1 mmol) of MTBD and 0.61 g (3.1 mmol) of 2-ethylhexyl bromide. The vial was vortex mixed to form a clear solution and placed in an oven at 104° C., removed and briefly vortex mixed after 14 minutes then returned to the oven. The contents were hazy/opaque after 14 minutes. An additional vortex mix was completed after 30 minutes. The vial was removed from the oven after 138 minutes. The contents separated into two phases, a thick lower phase and a thinner upper phase. $^1$H NMR showed the upper phase to be a mixture of starting materials and 2-ethylhexene. The crude material lower phase was evaluated as a phase transfer catalyst without purification.

Reference Example 3

DBU Octyl Bromine Quat

To a 500 ml 3 neck flask were added 193.67 g (1.00 mol) of 1-bromooctane. The flask was equipped with a paddle stirrer (202 rpm), a thermometer/$N_2$ headspace purge inlet, a water cooled reflux condenser/$N_2$ headspace purge outlet to oil filled bubbler and an addition funnel containing 152.73 g (1.00 mol) of DBU. The 1-bromooctane was heated with a heating mantle to 87° C. before the contents of the addition funnel were added drop-wise over 30 minutes. The contents were cooled to 80° C. before transfer to a bottle. In a separate experiment, the order of addition was reversed and found to be inconsequential. $^1$H NMR showed only a trace (~2 mol %) of 1-octene was formed and no starting material remained. The material was evaluated as a phase transfer catalyst without purification.

Reference Example 4

DBU Octyl Chloride Quat

To a 100 ml 3 neck flask were added 21.28 g (0.140 mol) of DBU and 20.77 g (0.140 mol) of 1-chlorooctane. The flask was equipped with a 1" magnetic stir bar, a thermometer/$N_2$ headspace purge inlet, and a water cooled reflux condenser/$N_2$ headspace purge outlet to oil filled bubbler. The contents were heated with a heating mantle and maintained at 120° C. for 3.3 hours. The contents were cooled to 80° C. before transfer to a bottle. $^1$H NMR showed only a trace (~2 mol %) of 1-octene was formed and no starting material remained. The material was evaluated as a phase transfer catalyst without purification.

Reference Example 5

MTBD Butyl Bromide Quat

At the ambient temperature, 1.80 g (11.3 mmol) of MTBD was mixed with 1.61 g (11.7 mmol) of 1-bromobutane. The reaction mixture was heated at 100° C. for 1 hour. After cooling down to the ambient temperature, a high viscosity dark-yellow clear liquid was isolated as the product. The product was analyzed with $^1$H NMR to verify that 1-bromobutane and MTBD were both reacted.

Reference Example 6

MTBD Octyl Bromide Quat

At the ambient temperature, 1.80 g (11.3 mmol) of MTBD was mixed with 2.26 g (11.7 mmol) of 1-bromooctane. The reaction mixture was heated at 100° C. for 1 hour. After cooling down to the ambient temperature, a high viscosity dark-yellow clear liquid was isolated as the product. The product was analyzed with $^1$H NMR to verify that 1-bromooctane and MTBD were both reacted. 1-Octene was detected at 4.8 mol % or 1.6 wt % content in the product.

Reference Example 7

MTBD Dodecyl Bromide Quat

At the ambient temperature, 1.60 g (10.4 mmol) of MTBD was mixed with 2.60 g (10.4 mmol) of 1-bromododecane. The reaction mixture was heated at 100° C. for 1 hour to form a viscous dark-yellow clear liquid. After cooling down to the ambient temperature, a yellow solid was isolated as the product. The product was analyzed with $^1$H NMR to verify that 1-bromododecane and MTBD were both reacted. 1-Dodecene was detected at 11.8 mol % or 5.3% content in the product.

Example 1

Synthesis of Bis(Triethoxysilylpropyl)Fumarate Using Different Phase Transfer Catalysts Model Reaction Scheme 1. Synthesis of bis(triethoxysilylproply) fumarate during the condensation of chloropropyltriethoxysilane and disodium fumarate.

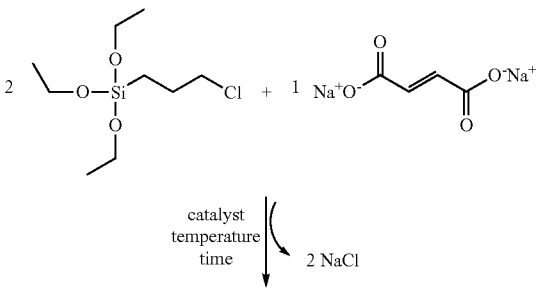

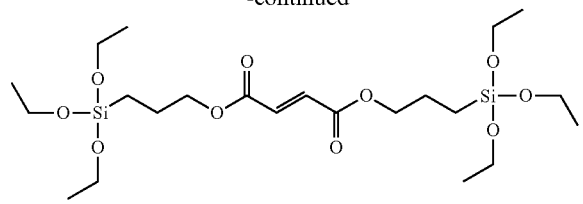

Bis(triethoxysilylpropyl)fumarate was synthesized with a selection of phase transfer catalysts (PTC) during the condensation of CPTES and disodium fumarate. The condensation reaction was performed by catalyzing the reaction of chloropropyltriethoxysilane (2.38 mL, 10 mmol) and disodium fumarate (0.80 g, 5 mmol) with a selection of catalysts shown below in Table 1-1. Each sample was formulated with amounts of CPTES and PTC at a ratio of 20:1 (CPTES:PTC ratio, mmol:mmol) or 5 mole % PTC. The reactions were conducted at temperatures ranging from 120° C. to 140° C. for 6 to 18 hours. The closed reactions were conducted in borosilicate glass with overhead stirring at 300 rpm at ambient pressure. The resultant reaction product was a liquid with a salt precipitate, which was quantified by Gas Chromatography under the conditions in Table 1-2.

The GC analysis was performed with a Hewlett-Packard 6890 Series injector on an HP 6890 plus gas chromatograph with a flame ionization detector (FID). The system was configured as detailed in Table 1-3.

dard was introduced after the reaction at approximately 5% from a solution of dodecane and toluene. Theoretical response factors for the analytes were calculated and entered into the ChemStation to automatically create a calibration table and quantitatively calculate the concentration of an analyte in the presence of an internal standard (Equation 1).

$$RF_{analyte} = ([analyte]/Area_{analyte}) \times (Area_{IS}/[IS]) \times RF_{IS} \quad \text{(Equation 1)}$$

The terms in Equation 1 are defined as follows: $RF_{analyte}$=theoretical response factor for the analyte, [analyte]=concentration of the analyte, $Area_{analyte}$=peak area of the analyte, $Area_{IS}$=peak area of the internal standard, [IS]= concentration of the internal standard, $RF_{IS}$=theoretical response factor for the internal standard.

The theoretical response factors used were 1.984 for bis(triethoxysilylpropyl)fumarate (bis-fumarate), 2.481 for the CPTES, and 1.181 for the dodecane.

The retention times of the materials of interest were 9.242 min for CPTES and 15.350 min for the bis-fumarate. Refer to Table 1-2. The CPTES and bis-fumarate peaks were confirmed by GC-MS.

Encompassing experimental and instrumental errors, the relative standard deviation of the measurements was less than 1%.

TABLE 1-3

| GC-FID Experimental Parameter Settings. | |
|---|---|
| Carrier gas | 99.9995% high purity helium |
| Detector | Flame ionisation detector at 280° C., $H_2$ = 30 mL/min, Air = 300 mL/min, Make up He = 45 mL/min |
| GC inlet, split | 275° C., split ratio = 100:1, constant pressure (rate = 1.0 mL/min) |
| GC column | HP-5MS crosslinked 5% phenyl methyl siloxane film (30 m x 0.25 mm, 0.25 um film) |
| GC temperature program | 55(3) to 300(5) @35° C./min, 15 minute total run time |
| Internal standard | ~22% (w/w) dodecane in phenylsilane |
| data system | Agilent Technologies ChemStation |

Dodecane was used as an internal standard to gravimetrically quantify the chromatographic analyses. Internal stan-

TABLE 1-1

| Phase Transfer Catalysts. | | | |
|---|---|---|---|
| Catalyst | Catalyst Source | Amount (0.5 mmol) | CPTES:Catalyst |
| 1,8-Diazabicyclo[5.4.0]undec-7-ene; DBU | Aldrich | 76.1 mg | 20:1 mmol/mmol |
| DBU-Octyl Bromine Quat | Reference Example 3 | 172.7 mg | 20:1 mmol/mmol |
| DBU-Octyl Bromine/Potassium acetate, 1:1 mol | Mixture of the quat prepared in Reference Example 3 and & KAc purchased from Aldrich | 172.7 + 49.0 mg | 20:1 mmol/mmol |
| Tetrabutylammonium bromide, TBAB | Aldrich | 161.3 mg | 20:1 mmol/mmol |
| Tetrabutylammonium acetate; TBA-Acetate | Aldrich | 150.8 mg | 20:1 mmol/mmol |
| Tetrabutylammonium chloride; TBA-Chloride | Aldrich | 139.0 mg | 20:1 mmol/mmol |
| Tetrabutylammonium hydrogenosulfate; TBA-Hydrogenosulfate | Aldrich | 169.8 mg | 20:1 mmol/mmol |
| Tetrabutylammonium bromide/Potassium acetate, 1:1 mol | Mixture of compounds purchased from Aldrich | 163.1 + 49.0 mg | 20:1 mmol/mmol |

"Aldrich" in the table above refers to Sigma-Aldrich Inc.

TABLE 1-2

PTC-catalyzed Synthesis of Bis(triethoxysilylpropyl) Fumarate (mg/mL).

| Catalyst | 140° C., 6 h | 120° C., 18 h |
|---|---|---|
| 1,8-Diazabicyclo[5.4.0]undec-7-ene (DBU) | 502 | 299 |
| DBU-Octyl Bromide Quat | 634 | 498 |
| DBU-Octyl Bromide/Potassium acetate, 1:1 mol | 885 | 509 |
| Tetrabutylammonium bromide, TBAB | 258 | 300 |
| Tetrabutylammonium acetate; TBA-Acetate | 263 | 325 |
| Tetrabutylammonium chloride; TBA-Chloride | 290 | 626 |
| Tetrabutylammonium hydrogenosulfate; TBA-Hydrogenosulfate | 404 | 648 |
| Tetrabutylammonium bromide/Potassium acetate, 1:1 mol | 192 | 278 |

Example 2

Synthesis of Bis(Triethoxysilyl Propyl)Fumarate with DBU

Disodium fumarate (93.0 g; 0.581 mol), CPTES (280.0 g; 1.16 mol), PTZ and BHT (0.112 g/each) and DBU (3.52 g) were sequentially added to a 500 ml round bottom (RB) flask equipped with a mechanical agitator. The reaction mixture was heated at 140° C. for 18 hr. After bodying by allowing the sample to stand for 2 days at ambient conditions, 191.3 g of clear brownish supernatant was decanted. Then 180 ml of hexanes was added to the salt residue to form a slurry. After forming the slurry, 480 g of 15% brine was added and mixed. After 30 min settlement, 224.5 g of clear organics were separated and vacuum stripped to give 82.6 g of a clear brownish liquid with low volatility. The two clear brownish liquids were combined and subject to a simple distillation under vacuum (less than 1 torr) at 140° C. The bis(triethoxysilylpropyl)fumarate product (238.3 g) was isolated in 92% yield. This example shows the speed and ease that the metal halide may be removed from bis(triethoxysilylpropyl)fumarate using the process of the invention.

Example 3

Comparison of Different PTCs

The phase transfer catalysis reaction between disodium fumarate and CPTES was found to be an effective synthetic route for making bis(3-triethoxysilylpropyl)fumarate. The reaction was a solid-liquid bi-phasic nucleophilic substitution. It was sluggish due to inefficient material transfer through the solid-liquid interface or interphase. To gain an acceptable conversion, a high reaction temperature and a prolonged reaction time were employed. Under these conditions, choice of catalyst and solvent affected the reaction rate.

The effects of the catalysts and solvents were studied using the following general experimental procedure.

1) Under a nitrogen blanket, to a 150 mL RB flask were loaded disodium fumarate and CPTES at 1:2 molar ratio, 500 ppm of BHT and PTZ stabilizers, a phase transfer catalyst, and optionally, a solvent.
2) The reaction mixture was heated to 140° C. under agitation.
3) The liquid phase was sampled for GC analysis after 3 h and 18 h. The GC peak areas of bis(3-triethoxysilylpropyl)fumarate and CPTES were used to calculate the GC area % of bis(3-triethoxysilylpropyl)fumarate using the equation "GC Area % of Bis(3-triethoxysilylpropyl)fumarate=(GC Peak Area of Bis(3-triethoxysilylpropyl)fumarate)/(GC Peak Area of Bis(3-triethoxysilylpropyl)fumarate+GC Peak Area of CPTES)×100%".
4) Four PTC's, i.e., tetrabutylammonium bromide (TBAB) and tetrabutylphosphonium bromide (TBPB), which were both comparative; and DBU and DBU octyl bromine quat; and two solvents (mineral spirit and DMF), were evaluated in six runs. The catalysts were added at 2 mol % or 4 mol % of the moles of CPTES. Mineral spirit is a non-polar solvent. DMF is a polar aprotic solvent. The solvents were added at a certain percentage of the weight of the reaction mixture. The calculated GC area % of bis(3-triethoxysilylpropyl)fumarate is compiled in Table 3-1 below for these six runs. The GC area % was qualitatively aligned to the actual reaction conversion, but could not be treated equally as the reaction conversion because bis(3-triethoxysilylpropyl)fumarate and CPTES have different GC response factors and affinities with the solid salts. Bis(3-triethoxysilylpropyl)fumarate seemed to have a lower GC response factor, and a lower affinity with the solid salts, than CPTES.

TABLE 3-1

The GC area % of bis(3-triethoxysilylpropyl)fumarate at 140° C.

| Batch # | Catalyst | Solvents | GC Area % | |
|---|---|---|---|---|
| | | | 3 hr | 18 hr |
| 1 | 4 mol % TBAB | Mineral spirit at 43 wt % | 4.2 | n/a |
| 2 | 4 mol % TBAB | None | 10.8 | 5.0 |
| 3 | 2 mol % DBU | None | 9.0 | 33.0 |
| 4 | 2 mol % DBU | DMF at 27 wt % | 15.8 | 79.4 |
| 5 | 2 mol % TBPB | None | 11.2 | 35.8 |
| 6 | 2 mol % DBU octy Br quat | None | 0.033 | 47.8 |

All the GC area % values in 3 hours were low, suggesting that the reaction was sluggish even at 140° C. and in the presence of catalysts. When 4 mol % of TBAB was used as the catalyst in Batch 2, the GC area % of bis(3-triethoxysilylpropyl)fumarate decreased from 10.8% in 3 hours to 5.0% in 18 hours. This resulted from quick degradation of TBAB in the first 3 hours at 140° C., as evidenced with a strong GC signal of the degradation product, tributylamine. Thus, TBAB was not a suitable catalyst for synthesis of bis(3-triethoxysilylpropyl)fumarate under these conditions. In the non-polar solvent, mineral spirit, in Batch 1, the reaction rate was further reduced as the GC area % was only 4.2% after 3 hours. Thus, a non-polar solvent was deemed detrimental to the reaction rate under these conditions. When the high temperature catalyst TBPB was used in Batch 5, the conversion was comparable to that of TBAB in 3 hours, but much higher than that of TBAB in 18 hours, indicating that TBPB was a better catalyst than TBAB for preparation of bis(3-triethoxysilylpropyl)fumarate under these conditions. DBU gave similar GC area % as TBPB in both 3 and 18 hours in Batch 3, suggesting that DBU was as efficient as TBPB. When 2 mol % of DBU octyl bromine quat was used as the catalyst in Batch 6, the conversion was low in 3 hours, but higher than those of DBU and TBPB in 18 hours. Without wishing to be bound by theory it is thought that there probably was an activation mechanism for DBU octyl bromine quat, and once activated, it was more efficient than DBU and TBPB. The most significant conversion gain in this example was achieved by doing the DBU-catalyzed reaction in the high polarity aprotic solvent, DMF, in Batch 4. There was a marginal lead of the GC area % in 3 hours and a remarkable superiority in 18 hours. Without wishing to be bound by theory, it is thought that the high GC area % in 18 hours could be attributed to an increased reaction rate, and a reduced association of bis(3-triethoxysilylpropyl)fumarate and CPTES with the solid salts in DMF. Therefore, it is thought that a high temperature catalyst, a polar aprotic solvent, or a combination thereof, can be used to improve the reaction conversion.

Example 4

Purification of Bis(Triethoxysilylpropyl)Fumarate

Two batches of bis(triethoxysilylpropyl)fumarate prepared above in example 3, 3 and 6, were purified using a brine wash procedure as follows.
1) The reaction mixture was allowed to stand for 2 days at the room temperature. During the period, the salts settled to form a clean solid-liquid interface
2) After the clear brownish organics (the 1$^{st}$ portion of crude product) was decanted, hexanes was added to the resulting salt cake, and the mixture was re-slurrified. Then a brine was added to dissolve or partially dissolve the salts to form a saturated NaCl solution. Water can be used in place of the brine as long as the resultant brine phase is near saturation. The amount of hexanes should be sufficient to allow a quick liquid-liquid phase separation.
3) Once agitation stopped, the light organic phase quickly separated from the heavy brine phase to give a clean liquid-liquid interface within a few minutes.
4) The organic phase was evaporated under vacuum to remove hexanes, giving a brownish liquid (the second portion of crude product).
5) The two portions of crude product were combined and distilled at the pot temperature of 140° C. under vacuum (0.1 torr) to remove unreacted CPTES.
6) The product was isolated from the pot as a brownish low viscosity liquid. The purity of the product was determined with GC-FID, and verified with $^1$H NMR to be 95%. The $^1$H NMR spectrum has the key features, including the unique chemical shift of the protons on the fumarate double bond, of the $^1$H NMR of bis(3-trimethoxysilylpropyl)fumarate.
7) The structure of the bis(3-triethoxysilylpropyl)fumarate molecule was confirmed with $^{13}$C and $^{29}$Si NMR and GC-MS.

This resulted in the isolation of bis(3-triethoxysilylpropyl)fumarate with 95% purity in 92% yield in Batch 3, and in 91% yield in Batch 6. The impurities consisted of 3.8% of CPTES and 0.8% of the by-products identified with GC-MS.

INDUSTRIAL APPLICABILITY

It was surprisingly found that some of the phase transfer catalysts described herein as ingredient c), and/or the combination of the phase transfer catalyst of ingredient c) and the co-catalyst of ingredient d), can be used to produce a bis(alkoxysilylalkyl)fumarate, such as bis(triethoxysilylpropyl)fumarate, at a lower temperature and/or a faster reaction time than when conventional phase transfer catalysts are used. The catalysts described herein may also produce the bis(alkoxysilylalkyl)fumarate with fewer by-products than when hexaethylguanidinium bromide is used as the catalyst with the same haloalkyl, alkoxysilane and metal salt of a fumarate.

The invention claimed is:

1. A method for producing a reaction product comprising a bis(alkoxysilylorgano) dicarboxylate, where the method comprises: step 1) reacting a composition comprising:
   a) a haloorganoalkoxysilane,
   b) a dimetal salt of a dicarboxyl functional compound, and
   c) a phase transfer catalyst comprising 7-methyl-1,5,7-triazabicyclo[4.4.0]dec-5-ene, a quaternary iminium compound of a bicyclic amidine, or a combination thereof.

2. The method of claim 1, where step 1) is performed under substantially anhydrous conditions by heating at a reaction temperature up to 180° C. for a reaction time up to 18 h.

3. The method of claim 1, further comprising step 2): removing at least a portion of a metal halide formed as a by-product during step 1).

4. The method of claim 3, further comprising step 3): recovering the bis(alkoxysilylorgano)dicarboxylate.

5. The method of claim 4, where the bis(alkoxysilylorgano) dicarboxylate is a bis(alkoxysilylalkyl)fumarate.

6. The method of claim 5, where the bis(alkoxysilylalkyl) fumarate is bis(triethoxysilylpropyl)fumarate.

7. The method of claim 1, further comprising: drying one or more of the ingredients before step 1).

8. The method of claim 1, where the composition further comprises an optional ingredient selected from the group consisting of d) a co-catalyst, e) a solvent, f) a stabilizer, and a combination thereof.

9. The method of claim 8, where the co-catalyst comprises a compound of formula: $M^+R^9$, where $M^+$ is an alkali metal cation or alkaline earth metal cation; and $R^9$ is a counter ion selected from the group consisting of $HSO_4^-$, $HCO_3^-$, acetate, $SO_4^{2-}$, $CO_3^{2-}$ and $PO_4^{3-}$.

10. The method of claim 2, where the reaction temperature ranges from 130° C. to 180° C., and the reaction time is up to 12 hours.

11. The method of claim 1, where ingredient c) comprises a quaternary iminium compound of a bicyclic amidine.

12. The method of claim 11, where ingredient c) comprises a 1,8-diazabicyclo[5.4.0]undec-7-ene quaternary iminium salt with octyl bromine; a 1,8-diazabicyclo[5.4.0]undec-7-ene quaternary iminium salt with ethylhexyl bromine; a 1,8-diazabicyclo[5.4.0]undec-7-ene quaternary iminium salt with octyl chlorine; 7-methyl-1,5,7-triazabicyclo[4.4.0]dec-5-ene quaternary iminium salt with ethylhexylbromine; 7-methyl-1,5,7-triazabicyclo[4.4.0]dec-5-ene quaternary iminium salt with butyl bromine; 7-methyl-1,5,7-triazabicyclo[4.4.0]dec-5-ene quaternary iminium salt with octyl bromine; 7-methyl-1,5,7-triazabicyclo[4.4.0]dec-5-ene quaternary iminium salt with dodecyl bromine; or a combination thereof.

13. The method of claim 11, where the composition further comprises a metal acetate.

14. The method of claim 1, where ingredient a) has formula (I):

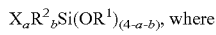

subscript a is 1 or 2;
subscript b is 0, 1, or 2;
each X is independently a halogenated organic group;
each $R^1$ is independently a hydrocarbyl group; and
each $R^2$ is independently a hydrocarbyl group.

15. The method of claim 1 where, ingredient b) has formula (II):

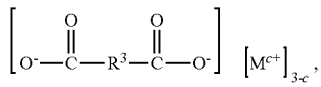

where
$M^+$ is an alkali metal cation or alkaline earth metal cation,
subscript c is 1 or 2, and
$R^3$ is a divalent organic group.

16. The bis(alkoxysilylorgano) dicarboxylate prepared by the method of claim 1.

17. A rubber composition suitable for use in tire applications, where the rubber composition comprises:
   A) a diene polymer,
   B) a reinforcing filler, and
   C) a bis(alkoxysilylalkyl)fumarate prepared by the method of claim 5.

18. A rubber composition suitable for use in engineered rubber goods applications, where the rubber composition comprises:
   A) a diene polymer,
   B) a reinforcing filler, and
   C) a bis(alkoxysilylalkyl) fumarate prepared by the method of claim 5.

19. The method of claim 1, further comprising: using the bis(alkoxysilylorgano) dicarboxylate for an application selected from the group consisting of a coupling agent, an adhesion promoter, and a surface modifier.

20. A method for producing a reaction product comprising a bis(alkoxysilylorgano) dicarboxylate, where the method comprises: step 1) reacting a composition comprising:
   a) a haloorganoalkoxysilane,
   b) a dimetal salt of a dicarboxyl functional compound,
   c) a phase transfer catalyst comprising a bicyclic amidine, a quaternary iminium compound of a bicyclic amidine, or a combination thereof, and
   d) a co-catalyst.

21. The method of claim 20, where the co-catalyst comprises a compound of formula: $M^+R^9$, where $M^+$ is alkali metal cation or alkaline earth metal cation; and $R^9$ is a counter ion selected from the group consisting of $HSO_4^-$, $HCO_3^-$, acetate, $SO_4^{2-}$, $CO_3^{2-}$ and $PO_4^{3-}$.

* * * * *